United States Patent [19]

Bregen

[11] Patent Number: 5,304,204
[45] Date of Patent: Apr. 19, 1994

[54] RECEIVERLESS SURGICAL FASTENERS

[75] Inventor: Michael F. Bregen, Lebanon, N.J.

[73] Assignee: Ethicon, Inc., Somerville, N.J.

[21] Appl. No.: 15,707

[22] Filed: Feb. 9, 1993

[51] Int. Cl.5 ............................................. A61B 17/00
[52] U.S. Cl. ................................. 606/219; 411/904;
411/457; 411/920
[58] Field of Search ....................... 606/219, 220, 221;
411/457, 920, 904

[56] References Cited

U.S. PATENT DOCUMENTS 4,719,917  1/1988  Barrows ............................... 411/457
5,158,566  10/1992  Pianetti ................................ 606/221

Primary Examiner—Stephen C. Pellegrino
Assistant Examiner—Gary Jackson
Attorney, Agent, or Firm—Paul A. Coletti; Charles P. Boukus

[57] ABSTRACT

A self-closing receiverless surgical fastener comprises a fastener body of biocompatible or bioabsorbable material including a bridge member and at least two tines extending from opposite ends of the bridge member. The tines are resiliently deformable from a normally closed position with the distal ends of the tines pointing toward each other to an open position with the distal ends of the tines extending substantially parallel to each other for penetrating into tissue. The tines are resiliently returnable to the closed position with the distal ends of the tines pointing toward each other to secure the fastener body to the tissue.

22 Claims, 2 Drawing Sheets

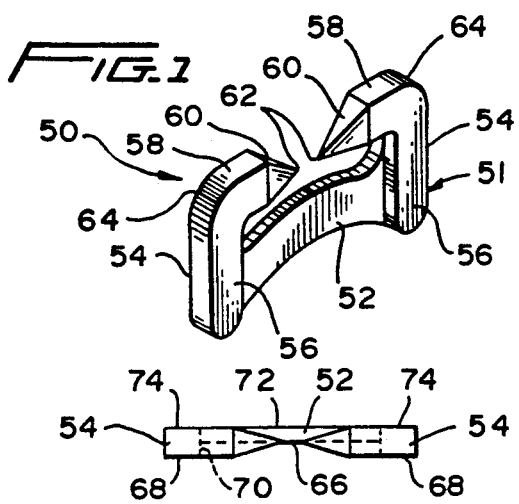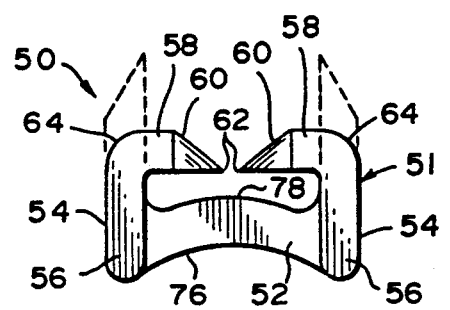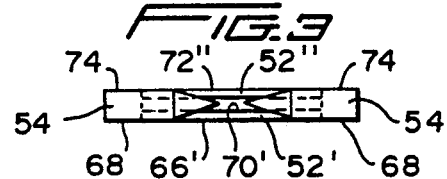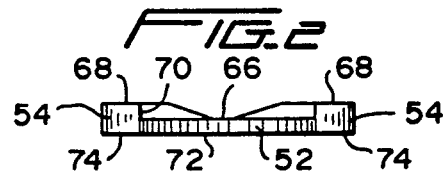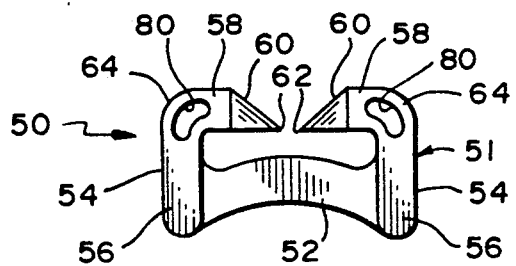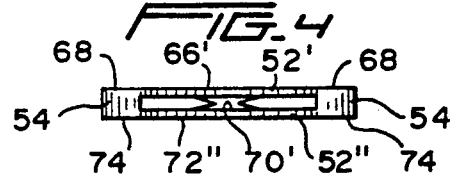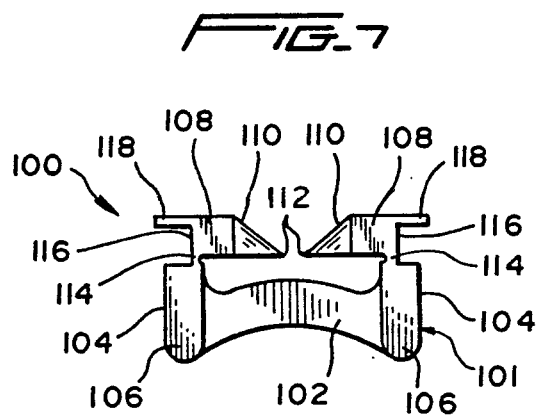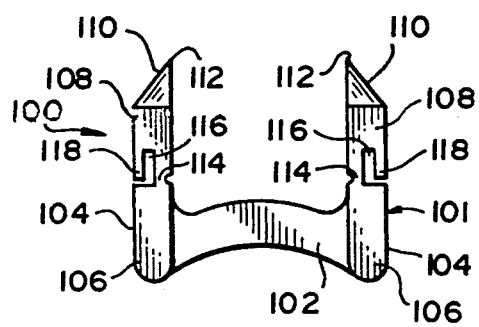

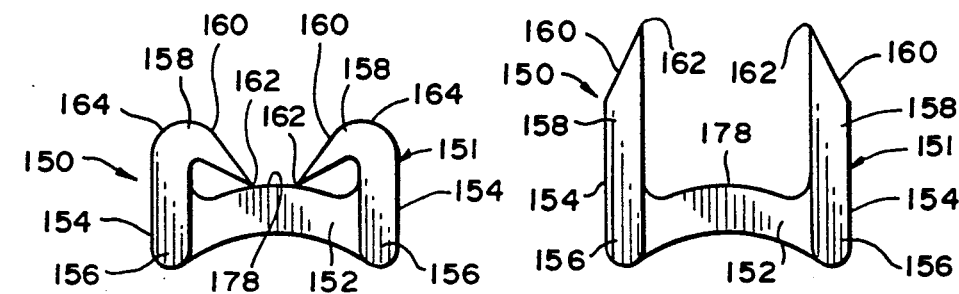
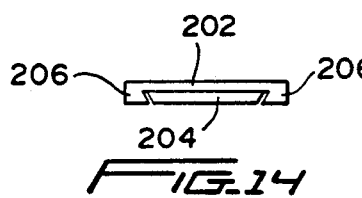
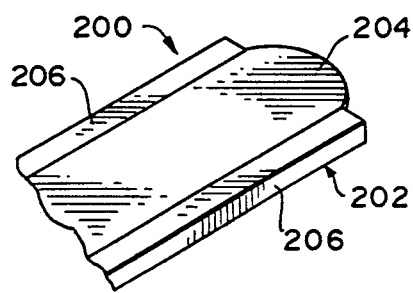
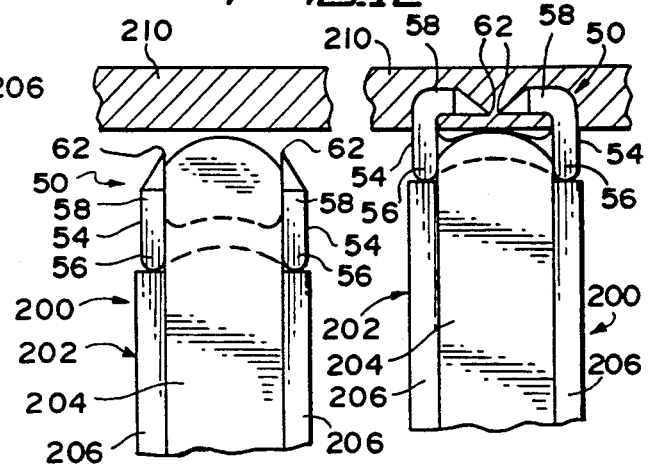
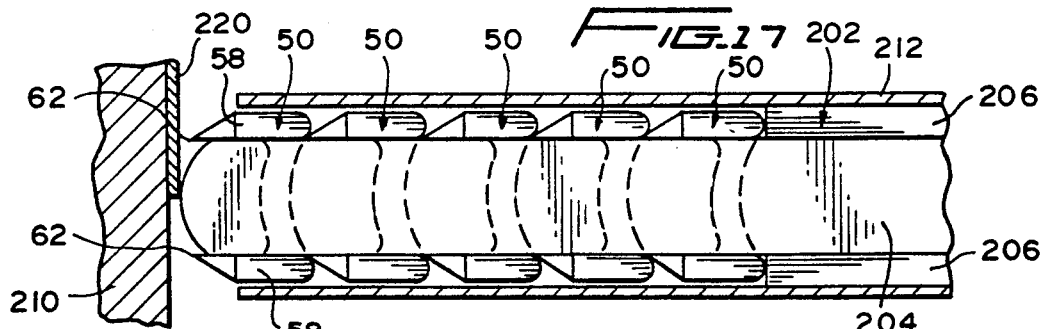
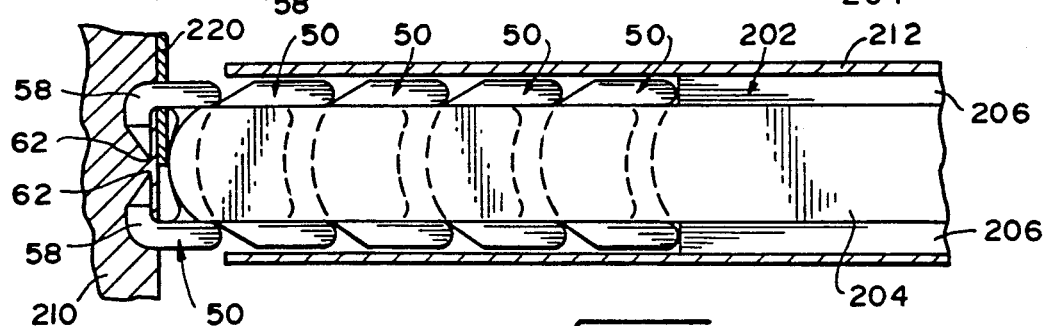

//  5,304,204

RECEIVERLESS SURGICAL FASTENERS

FIELD OF THE INVENTION

The present invention relates to a surgical fastener and, more particularly, to a surgical fastener of biocompatible or bioabsorbable material which is adapted to secure a hernia patch to internal body tissue.

BACKGROUND OF THE INVENTION AND PRIOR ART

Surgical fasteners, or staples, are commonly used in surgical procedures to allow a surgeon to fasten body tissue together without the need for time consuming suturing procedures. The surgical fasteners can be applied to the body tissue by using surgical staplers which operate to install the fasteners one at a time or to apply a plurality of fasteners in succession or simultaneously. The staplers typically include fastener cartridges from which the fasteners are driven into the tissue.

Two-part surgical fastener devices are previously known. Such devices include a fastener member, or staple, which is generally U-shaped in configuration with a pair of prongs, and a receiver member provided with apertures in which the prongs are engaged and latched. The fastener prongs pierce the body tissue from one side and the receiver member latches the prongs on the other side of the tissue. The surgical fasteners, once engaged, are not separable so that, after being inserted into the body tissue, the fasteners cannot be easily removed. Accordingly, two-part surgical fasteners usually consist of bioabsorbable material which is absorbed into the body tissue.

In the past, hernia repair procedures have been performed by open surgery in which an elongated incision is made in the body wall for access to the internal body tissue to be repaired. Such open surgery is traumatic to the patient and a long recovery period is required for the incision to heal. Typically, the hernia repair is performed by conventional suturing techniques. A hernia repair patch, if used, is secured to the internal body tissue by sutures applied along the edges of the patch.

More recently, endoscopic instruments and techniques have been developed to perform surgery on internal body tissue, including hernia repairs. Such procedures are performed by installing an endoscopic tube in a small incision in the body wall and by inserting the surgical instruments into the endoscopic tube to perform the desired surgery. The endoscopic procedures are less traumatic to the patient and result in a shorter recovery period in comparison with open surgery.

In performing hernia repairs by endoscopic surgery, it is necessary to employ surgical fasteners or staples which are capable of securely holding the internal body tissue together. Also, if a hernia patch is installed, the surgical fasteners or staples must be capable of securely fastening the hernia patch to the internal body tissue. The endoscopic instruments previously used for hernia repair procedures have utilized surgical fasteners or staples made of metal, e.g., titanium or stainless steel. These instruments generally include a staple forming mechanism which forms the surgical fastener from an open position to a closed position penetrating the tissue at the surgical site.

The metal fasteners or staples previously used for hernia repairs remain permanently inside the patient and are not absorbed by the internal body tissue. Such metal fasteners or staples are opaque to x-rays and appear in x-ray photographs of the patient. Thus, it is desirable to employ surgical fasteners or staples of bioabsorbable material for hernia repairs because the fasteners or staples are eventually absorbed into the body tissue and do not interfere with x-ray photographs of the patient. The previous two-part surgical fasteners of bioabsorbable material tend not to be suitable for hernia repairs because of the difficulty of obtaining the access to both sides of the tissue to be repaired. Accordingly, a receiverless fastener of bioabsorbable material is highly desirable for hernia repairs and other surgical procedures on internal body tissue. Also, it is advantageous to provide a self-closing receiverless fastener which avoids the need for using a surgical instrument with a forming mechanism to secure the fastener to internal body tissue.

SUMMARY OF THE INVENTION

Accordingly, it is an object of the present invention to provide a surgical fastener of biocompatible or bioabsorbable material which is useful for hernia repairs and other surgical procedures on internal body tissue.

It is also an object of the invention to provide a receiverless surgical fastener of biocompatible or bioabsorbable material which is suitable for use in endoscopic procedures to perform hernia repairs or other surgery on internal body tissue.

Another object of the invention is to provide a receiverless surgical fastener of biocompatible or bioabsorbable material which is capable of securely fastening a hernia patch to the internal body tissue.

It is another object of the invention to provide a receiverless surgical fastener or staple of resilient biocompatible or bioabsorbable material which is self-closing and can be applied to internal body tissue by endoscopic instruments without the need for staple forming mechanisms.

A further object of the invention is to provide a receiverless surgical fastener which can be applied to internal body tissue by an applicator capable of delivering and applying a single surgical fastener or a series of surgical fasteners in succession to the body tissue.

In accordance with the present invention, a surgical fastener comprises a fastener body including a bridge member and at least two tines extending from opposite ends of the bridge member, the tines each having a distal end for penetrating tissue, the tines being resiliently deformable from a normally closed position with the distal ends of the tines pointing toward each other to an open position with the distal ends of the tines extending substantially parallel to each other for penetrating into the tissue, and the tines being resiliently returnable to the closed position with the distal ends of the tines pointing toward each other to secure the fastener body to the tissue. Preferably, each of the tines has a resilient hinge-like section which normally maintains the distal ends of the tines pointing toward each other. The resilient hinge-like sections permit the distal ends of the tines to pivot from a closed position pointing toward each other to an open position substantially parallel to each other.

In accordance with another aspect of the invention, a surgical fastener comprises a fastener body including a bridge member and at least two tines extending in the same direction from opposite ends of the bridge member, the tines including proximal portions extending substantially parallel to each other from the bridge member and distal portions extending transversely from the proximal portions and pointing toward each other, the distal portions of the tines being movable in response to pressure to a substantially parallel orientation to each other, and the distal portions of the tines being resiliently returnable to a transverse orientation pointing toward each other when the pressure is released. Preferably, the fastener body consists of resilient material which is biocompatible or bioabsorbable.

In a preferred embodiment of the surgical fastener, the bridge member is curved in shape and extends between the proximal ends of the tines. The bridge member is reduced in thickness compared with the tines for slidably receiving an actuator between the tines to apply pressure to pivot the distal ends of the tines. Alternatively, a pair of bridge members is arranged side by side and spaced apart for slidably receiving an actuator therebetween to apply pressure to pivot the distal ends of the tines.

BRIEF DESCRIPTION OF THE DRAWINGS

The foregoing and other objects, aspects and advantages will be better understood from the following detailed description of the preferred embodiments of the invention with reference to the drawings, in which:

FIG. 1 is a perspective view of a surgical fastener constructed in accordance with the present invention;

FIG. 2 is a front elevation of the surgical fastener of FIG. 1;

FIG. 3 is a top plan view of the surgical fastener of FIG. 1;

FIG. 4 is a bottom plan view of the surgical fastener of FIG. 1;

FIG. 5 is a top plan view of a modified embodiment of the surgical fastener of FIG. 1;

FIG. 6 is a bottom plan view of the surgical fastener of FIG. 5;

FIG. 7 is a front elevation of another embodiment of the surgical fastener in a closed position;

FIG. 8 is a front elevation of the surgical fastener of FIG. 7 in an open position;

FIG. 9 is a front elevation of another embodiment of the surgical fastener in a closed position;

FIG. 10 is a front elevation of the surgical fastener of FIG. 9 in an open position;

FIG. 11 is a front elevation of another embodiment of the surgical fastener in a closed position;

FIG. 12 is a front elevation of the surgical fastener of FIG. 11 in an open position;

FIG. 13 is a perspective view of an applicator used to install the surgical fasteners of the present invention;

FIG. 14 is a distal end view of the applicator of FIG. 13;

FIG. 15 illustrates the surgical fastener of FIG. 1 in an open position mounted at the distal end of the applicator;

FIG. 16 illustrates the surgical fastener of FIG. 1 in a closed position when the fastener is displaced from the distal end of the applicator;

FIG. 17 is a partially cutaway side view showing a series of surgical fasteners mounted on an applicator inserted into an endoscopic tube to secure a hernia patch to the body tissue; and FIG. 18 is a partially cutaway side view showing the operation of the applicator of FIG. 17 to displace the forwardmost surgical fastener to secure the hernia patch to the body tissue.

DETAILED DESCRIPTION OF PREFERRED EMBODIMENTS

Referring to FIG. 1, the present invention is embodied in a surgical fastener, generally 50, comprising a fastener body 51 including a bridge member 52 and a pair of tines 54 extending in the same direction from opposite ends of the bridge member 52. The tines 54 include proximal portions 56 extending substantially parallel to each other from the bridge member 52 and distal portions 58 extending transversely from the proximal portions 56 and pointing toward each other. The distal portion 58 of each tine 54 has a sloping surface 60 which terminates at a sharp tissue penetrating point 62. Each tine 54 has a resilient hinge-like corner section 64 connecting the proximal portion 56 to the distal portion 58 of the tine 54.

In the surgical fastener 50 of FIGS. 1-4, the resilient nature of the material of the fastener body 51 provides the desired hinge-like action of the tines 54. The fastener material is sufficiently resilient to allow the distal portions 58 of the tines 54 to move in response to pressure on the inside of the tines 54 to a substantially parallel orientation to each other for penetration of the tissue. The hinge-like sections 64 allow the distal portions 58 of the tines 54 to be resiliently returned to a transverse orientation pointing toward each other (FIG. 2) when the pressure is released.

As shown in FIG. 2, the tines 54 are resiliently deformable from a normally closed position with the distal ends 58 of the tines 54 pointing toward each other to an open position with the distal ends 58 of the tines 54 extending substantially parallel to each other for penetrating into the tissue. The tines 54 are resiliently returnable to the closed position with the distal ends 58 of the tines 54 pointing toward each other to secure the fastener body 51 to the tissue. Thus, the surgical fastener 50 is self-closing because of the tendency of the resilient fastener material to return to its original shape.

In a preferred embodiment of the fastener 50, the fastener body 51 consists of resilient material which is biocompatible or bioabsorbable. As contemplated herein, biocompatible refers to a fastener material which can remain inside the human body without trauma or detrimental effects on the body tissue. The biocompatible material can be either absorbable or non-absorbable by the body tissue. If a non-absorbable fastener material is used, the surgical fastener remains permanently implanted in the body tissue. Bioabsorbable refers to a fastener material which is biocompatible and gradually absorbed into the body tissue so that the surgical fastener eventually disappears. Examples of bioabsorbable fastener materials are, but not limited to, absorbable polymers or copolymers such as polydioxidone, polyglycolic acid, polylactide glycoloid and polyglactin 910. It is further contemplated that any biocompatible or bioabsorable material of sufficient strength and resiliency can be used as the material for the surgical fasteners disclosed herein.

Preferably, the bridge member 52 is reduced in thickness compared with the tines 54. As shown in FIGS. 3 and 4, each tine 54 has a rectangular cross section and the thickness of the bridge member 52 is approximately one-half of the thickness of each tine 54. The bridge member 52 has a flat front surface 66 which is recessed from the front surfaces 68 of the tines 54 to provide a shallow channel 70 located between the tines 54 for receiving an applicator described below. The bridge member 52 has a flat rear surface 72 which is flush with the rear surfaces 74 of the tines 54.

As shown in FIGS. 1 and 2, the bridge member 52 is joined at its opposite ends to the inside of the proximal portions 56 of the tines 54. The central portion of the bridge member 52 is curved upwardly, i.e., in the proximal direction, to provide a lower concave edge 76 and an upper convex edge 78 on the bridge member 52.

Alternatively, as shown in FIGS. 5 and 6, the surgical fastener 50 may include front and rear bridge members 52' and 52'', respectively, which are arranged side by side and spaced apart to provide a channel 70' therebetween for receiving an applicator described below. The front bridge member 52' has a flat front surface 66' which is flush with the front surfaces 68 of the tines 54. The rear bridge member 52'' has a flat rear surface 72'' which is flush with the rear surfaces 74 of the tines 54.

As shown in FIGS. 1 and 2, the surgical fastener 50 normally assumes a closed position with the distal portions 58 of the tines 54 pointing toward each other. In response to pressure applied by an actuator inserted between the tines 54, the distal portions 58 are pivoted about the hinge-like corner sections 64, as indicated by the phantom lines of FIG. 2, into an open position with the distal portions 58 in a substantially parallel orientation to each other for insertion into the body tissue. When the pressure is released, the distal portions 58 of the tines 54 return to the closed position to secure the surgical fastener 50 to the body tissue.

Referring to FIGS. 7 and 8, in a modified embodiment of the surgical fastener 50, a curved or crescent-shaped opening 80 is formed at the hinge-like section 64 of each tine 54. Preferably, the openings 80 extend completely through the tines 54 from front to back. The crescent-shaped openings 80 enhance the resiliency of the hinge-like sections 64 and enhance the ability of the surgical fastener 50 to return to its closed position after the distal portions 58 of the tines 54 are flexed open and inserted into the body tissue.

Referring to FIGS. 9 and 10, the present invention is also embodied in a surgical fastener 100 comprising a fastener body 101 of resilient biocompatible or bioabsorbable material including a curved bridge member 102 with a pair of tines 104 extending in the same direction from opposite ends of the bridge member 102. The tines 104 include proximal portions 106 extending substantially parallel to each other from the bridge member 102 and distal portions 108 extending transversely from the proximal portions 106 and pointing toward each other. Each distal portion 108 of the tines 104 has a sloping surface 110 which terminates at a sharp tissue-penetrating point 112. Each tine 104 includes a resilient hinge-like section 114 connecting the proximal portion 106 to the distal portion 108 of the tine 104. Each distal portion 108 of the tine 104 is partially cutaway to provide a notch 116 which defines the hinge-like section 114.

As shown in FIG. 9, a tab 118 is formed on each distal portion 108 adjacent to the hinge-like section 114. The tabs 118 project laterally outward when the distal portions 108 of the tines 104 are pointing toward each other in the closed position of the surgical fastener 100. As shown in FIG. 10, when pressure is applied to pivot the distal portions 108 of the tines 104 into a substantially parallel orientation, the tabs 118 are received in the notches 116 formed in the sides of the tines 104. Also, when the surgical fastener 100 is inserted into an endoscopic tube, the tabs 118 are pressed inwardly by the interior wall of the endoscopic tube to force the distal portions 108 of the tines 104 to open for penetration into the body tissue. After the surgical fastener 100 is secured to the body tissue and returned to its closed position, the laterally projecting tabs 118 act as one-way barbs to force the distal portions 108 inwardly to provide a secure closure.

Referring FIGS. 11 and 12, the present invention is also embodied in a surgical fastener 150 comprising a fastener body 151 of resilient biocompatible or bioabsorbable material including a bridge member 152 and a pair of tines 154 extending in the same direction from opposite ends of the bridge member 152. The tines 154 include proximal portions 156 extending substantially parallel to each other from the bridge member 152 and distal portions 158 extending from the proximal portions 156 and pointing inward toward each other and toward the bridge member 152. Each distal portion 158 of the tines 156 has a sloping surface 160 which terminates in a sharp tissue-penetrating point 162. Each tine 154 has a resilient hinge-like corner section 164 connecting the proximal portion 156 to the distal portion 158 of the tines 154.

As shown in FIG. 11, the surgical fastener 150 normally assumes a closed position with the distal portions 158 of the tines 154 pointing toward each other and the tissue-penetrating points 162 engaging an upper convex edge or crown 178 of the bridge member 152. In response to pressure applied by an actuator inserted between the tines 154, the distal portions 158 are pivoted about the hinge-like sections 164 into a substantially parallel orientation to each other (FIG. 12) for insertion into the body tissue. When the pressure is released, the distal portions 158 of the tines 154 return to the closed position to secure the surgical fastener 150 to the body tissue.

Referring to FIGS. 13 and 14, an applicator, generally 200, for applying the surgical fasteners to the body tissue comprises an elongated channel-shaped pusher member 202 and an elongated flat tongue 204 which are slidable longitudinally relative to each other. As shown in FIG. 14, the tongue 204 has a trapezoidal cross section which is slidably received in dovetail fashion between a pair of flanges 206 extending longitudinally along opposite sides of the pusher member 202.

As shown in FIG. 15, to mount one of the surgical fasteners 50 on the applicator 200, the tongue 204 is extended beyond the distal end of the pusher member 202 and the distal end of the tongue 204 is inserted in the shallow channel 70 between the tines 54 to pivot the distal portions 58 of the tines 54 into an open position in a substantially parallel orientation to each other. The tongue 204 maintains the surgical fastener 50 in its open position with the tissue penetrating points 62 oriented parallel to each other. The distal end of the applicator 200 is positioned adjacent to a section of body tissue 210 to which the surgical fastener 50 is to be secured. Then, as shown in FIG. 16, the pusher member 202 is moved distally relative to the tongue 204 to engage the proximal portions 56 of the tines 54 to push the surgical fastener 50 distally away from the tongue 204. As the surgical fastener 50 is pushed in the distal direction, the tissue-penetrating tips 62 penetrate into the body tissue 210. Also, as the distal portions 58 of the tines 54 are disengaged from the tongue 204, the distal portions 58 return to the closed position pointing toward each other. As a result, the surgical fastener 50 is secured to the body tissue 210 by the distal portions 58 of the tines 54.

With respect to the embodiment of the surgical fastener 50 shown in FIGS. 5 and 6, the tongue 204 of the applicator 200 can be inserted into the channel 70' located between the bridge members 52' and 52" to apply the pressure to pivot the distal portions 58 of the tines 54 into an open position in a substantially parallel orientation to each other. Then, the pusher member 202 is moved distally relative to the tongue 204 to engage the distal portions 56 of the tines 54 to push the surgical fastener 50 distally away from the tongue 204. As the surgical fastener 50 is pushed in the distal direction, the tissue-penetrating tips 62 penetrate into the body tissue 210. When the distal portions 58 of the tines 54 are disengaged from the tongue 204, the distal portions 58 return to the closed position pointing toward each other to secure the fastener 50 to the body tissue 210.

Referring to FIGS. 17 and 18, a plurality of the surgical fasteners of the present invention can be applied in succession by the applicator 200 to fasten a hernia patch 220 to the body tissue 210. Preferably, the surgical fasteners are applied along the edges of the hernia patch 220.

As shown in FIG. 17, a series of surgical fasteners 50 is mounted end-to-end along the distal end of the tongue 204 of the applicator 200 which is inserted into an endoscopic tube 212. The applicator 200 and the endoscopic tube 212 are positioned at a desired surgical site to align the forwardmost staple 50 with the edge of the hernia patch 220. Then, as shown in FIG. 18, the pusher 202 is advanced to push the forwardmost staple 50 in the distal direction along the tongue 204. The forwardmost staple 50 is disengaged from the tongue 204 and the distal portions 58 of the tines 54 return to the closed position to secure the edge of the hernia patch 220 to the body tissue 210. Thereafter, the applicator 210 and the endoscopic tube 212 are moved to a different position along the edge of the hernia patch 220 where the operation of the applicator 200 is repeated to secure the next surgical fastener 50 to the body tissue 210.

In a similar fashion, the applicator 200 can be used to apply the modified embodiment of the surgical fastener 50 shown in FIGS. 7 and 8. In addition, the applicator 200 can be used to apply the surgical fastener 100 of FIGS. 9-10 and the surgical fastener 150 of FIGS. 11-12.

The invention in its broader aspects is not limited to the specific details of the preferred embodiments shown and described, and those skilled in the art will recognize that the invention can be practiced with modification within the spirit and scope of the appended claims.

I claim:

1. A surgical fastener, comprising:
a fastener body including a bridge member and at least two tines extending from opposite ends of said bridge member, said tines each having a distal end for penetrating tissue;
said tines being resiliently deformable from a normally closed position with said distal ends of said tines pointing toward each other to an open position with said distal ends of said tines extending substantially parallel to each other for penetrating into the tissue; and
said tines being resiliently returnable to said closed position with said distal ends of said tines pointing toward each other to secure said fastener body to the tissue.

2. The surgical fastener of claim 1, wherein:
said fastener body consists of resilient material.
3. The surgical fastener of claim 1, wherein:
said fastener body consists of biocompatible material.
4. The surgical fastener of claim 1, wherein:
said fastener body consists of bioabsorbable material.
5. The surgical fastener of claim 1, wherein:
each of said tines has a resilient hinge-like section which normally maintains said distal ends of said tines pointing toward each other.
6. The surgical fastener of claim 5, wherein:
said resilient hinge-like sections permit said distal ends of said tines to pivot from a closed position pointing toward each other to an open position substantially parallel to each other.
7. The surgical fastener of claim 5, wherein:
each tine has a tab adjacent to said hinge-like section which projects laterally outward when said distal ends of said tines are pointing toward each other.
8. The surgical fastener of claim 5, wherein:
a portion of each tine is removed adjacent to said hinge-like section to enhance the resiliency of said tines.
9. The surgical fastener of claim 1, wherein:
said bridge member is curved in shape and extends between the proximal ends of said tines.
10. The surgical fastener of claim 1, wherein:
said bridge member is reduced in thickness compared with said tines for slidably receiving an actuator between said tines to apply pressure to pivot said distal ends of said tines.
11. The surgical fastener of claim 1, wherein said bridge member comprises:
a pair of bridge members arranged side by side and spaced apart for slidably receiving an actuator therebetween to apply pressure to pivot said distal ends of said tines.
12. A surgical fastener, comprising:
a fastener body including a bridge member and at least two tines extending in the same direction from opposite ends of said bridge member;
said tines including proximal portions extending substantially parallel to each other from said bridge member and distal portions extending transversely from said proximal portions and pointing toward each other;
said distal portions of said tines being movable in response to pressure to a substantially parallel orientation to each other, and said distal portions of said tines being resiliently returnable to a transverse orientation pointing toward each other when said pressure is released.
13. The surgical fastener of claim 12, wherein:
said fastener body consists of resilient material.
14. The surgical fastener of claim 12, wherein:
said fastener body consists of biocompatible material.
15. The surgical fastener of claim 12, wherein:
said fastener body consists of bioabsorbable material.
16. The surgical fastener of claim 12, wherein:
each of said tines has a resilient hinge-like section which normally maintains said distal ends of said tines pointing toward each other.
17. The surgical fastener of claim 16, wherein:
said resilient hinge-like sections permit said distal ends of said tines to pivot from a closed position pointing toward each other to an open position substantially parallel to each other.
18. The surgical fastener of claim 16, wherein:

each tine has a tab adjacent to said hinge-like section which projects laterally outward when said distal ends of said tines are pointing toward each other.

19. The surgical fastener of claim 16, wherein:
a portion of each tine is removed adjacent to said hinge-like section to enhance the resiliency of said tines.

20. The surgical fastener of claim 12, wherein:
said bridge member is curved in shape and extends between the proximal ends of said tines.

21. The surgical fastener of claim 12, wherein: said bridge member is reduced in thickness compared with said tines for slidably receiving an actuator between said tines to apply pressure to pivot said distal ends of said tines.

22. The surgical fastener of claim 12, wherein said bridge member comprises:
a pair of bridge members arranged side by side and spaced apart for slidably receiving an actuator therebetween to apply pressure to pivot said distal ends of said tines.

* * * * *